(12) United States Patent
Carlson et al.

(10) Patent No.: US 9,860,382 B2
(45) Date of Patent: Jan. 2, 2018

(54) SYSTEMS AND METHODS FOR PREDICTIVE PERSONALIZATION AND INTELLIGENT ROUTING

(71) Applicant: UnitedHealth Group Incorporated, Minnetonka, MN (US)

(72) Inventors: Christopher Carlson, Dayton, MN (US); Sean McNattin, Dayton, MN (US); Jeffery Greely, Chanhassen, MN (US); Michael T. Barnes, Daleville, VA (US); Sandra Long, St. Paul, MN (US); Heather Winter Look, Bloomington, MN (US)

(73) Assignee: UnitedHealth Group Incorporated, Minnetonka (*) Notice: Subject to any disclaimer, the term of this patent is extended or adjusted under 35 U.S.C. 154(b) by 0 days.

(21) Appl. No.: 14/936,874

(22) Filed: Nov. 10, 2015

(65) Prior Publication Data
US 2016/0134755 A1 May 12, 2016

Related U.S. Application Data

(60) Provisional application No. 62/077,488, filed on Nov. 10, 2014.

(51) Int. Cl.
*H04M 3/00* (2006.01)
*H04M 3/523* (2006.01)
*H04M 3/51* (2006.01)
*G06F 19/00* (2011.01)

(52) U.S. Cl.
CPC ...... *H04M 3/5233* (2013.01); *G06F 19/3425* (2013.01); *H04M 3/5166* (2013.01); *G06F 19/327* (2013.01); *H04M 2201/40* (2013.01)

(58) Field of Classification Search
CPC .................................................. H04M 3/5158
USPC ....... 379/265.01–265.14, 266.01–266.1, 309
See application file for complete search history.

(56) References Cited

U.S. PATENT DOCUMENTS

| | | |
|---|---|---|
| 2002/0136381 A1 | 9/2002 | Shaffer et al. |
| 2007/0198249 A1* | 8/2007 | Adachi ............... G06F 17/2705 704/9 |
| 2008/0095355 A1 | 4/2008 | Mahalaha et al. |
| 2009/0136012 A1 | 5/2009 | Boyd et al. |
| 2014/0143197 A1* | 5/2014 | Schvekher ........ G06F 17/30483 706/46 |
| 2015/0081290 A1* | 3/2015 | Tremblay ............ G10L 15/1815 704/231 |

(Continued)

OTHER PUBLICATIONS

International Search Report from PCT/US2015/059879.

*Primary Examiner* — William Deane, Jr.
(74) *Attorney, Agent, or Firm* — Seyfarth Shaw LLP; Brian Michaelis

(57) ABSTRACT

Systems and methods for intelligently routing a member of an organization to a single point-of-contact within an optimized, secure network to address all the member's healthcare needs are described. The disclosed intelligent routing configurations transform and process, in real-time, vast amounts of member data to generate specialized effort scores specific to each member's household. The effort scores, among other things, are used to determine an appropriate tier within the organization to route the member, and its account file containing real-time member and household level data.

17 Claims, 11 Drawing Sheets

(56) References Cited

U.S. PATENT DOCUMENTS

2015/0156327 A1\* 6/2015 Van Buren .......... H04M 3/4936
 370/352
2016/0203500 A1\* 7/2016 Williams ........... G06Q 30/0203
 705/7.32

\* cited by examiner

SYSTEMS AND METHODS FOR PREDICTIVE PERSONALIZATION AND INTELLIGENT ROUTING

CROSS-REFERENCE TO RELATED APPLICATION DATA

This application claims priority to U.S. Provisional Patent Application Ser. No. 62/077,488, which is incorporated herein by reference in its entirety.

FIELD OF TECHNOLOGY

The present disclosure relates generally to secure networks, and more particularly to intelligent routing of data within a network.

BACKGROUND

Individuals contact organizations on a daily basis for a variety of reasons. In the past, organization representatives received and routed calls based on verbal caller input. Nowadays, however, organizations routinely have network with automated systems that receive and route calls within the network. The automated systems sometimes use natural language or intelligent routing technologies that route incoming calls using data and/or voice input of a caller.

Current technologies may use caller ID and natural language technologies to route a call to a specific representative group of an organization. However, current technologies do not provide organization representatives with intelligent routing coupled with broad access to caller data in real-time. Known systems are generally not designed and configured in a manner to adequately capture and translate the service needs of a caller while routing calls and data.

For example, callers typically have concerns or issues that require analysis by many points of contact across an organization. These points of contact are often disparate and disconnected, requiring a caller to call many areas of an organization or the caller be re-directed several times before having their problems adequately addressed by appropriate resources within the organization.

SUMMARY

The present disclosure generally provides systems and methods that solve the technical problems associated with limited intelligence and data association applied in routing of calls, such as processed through Interactive Voice Response IVR) systems, within an organization. Improved systems and methods according to the disclosure use an automatic number identification processor (ANI), an improved conversation management processor (CM), and natural language processor to provide an organization member with a single organization point-of-contact within an optimized network to address all the member's needs. The member and their household are identified using ANI or other authentication techniques, the caller's expressed, explicit need is identified using natural language processing techniques, and the member's implicit, anticipated needs are derived by the CM using associated data sources and a variety of independent analytic variables.

The CM includes a specially configured and tailored rules engine that filters data inputs from several data sources. The CM specifically applies rules to the data and determines the implicit or anticipated level, e.g., basic, complex, or clinical in nature, of call messaging presentation and representative/advocate support most appropriate for the member.

A member may contact the organization on behalf of themselves or another member of their household. Thus, the present disclosure provides for identification of the needs of all identifiable individuals of the member's household, thereby preventing the need to transfer the member to various organization advocates until all of the member's needs are addressed or resolved. Specifically, the systems and methodology disclosed herein enable the single organization point-of-contact within the optimized network to address all of a member's needs by providing the organization advocate with an exhaustive real-time record and tailored graphical user interface (GUI) encompassing data associated with all individuals of the member's household.

The improved conversation management processor of the present disclosure provides a cross-channel member engagement solution that maintains a holistic, contextual record for each member, thereby allowing for quick and effective placement of a member with an appropriate organization advocate. This prevents various member complaints experienced under present technologies. The disclosed system and method avoids dropping of information, i.e. information collected during an interactive voice response not being transferred to the ultimate organization advocate. The disclosed system and method avoids long and confusing prompts and inadequate menu options for directing the member to the appropriate organization advocate. Similarly, the disclosed system and method avoids the ultimate advocate misunderstanding the context of the member's call.

The specific, sophisticated analytics performed by the intelligent conversation management processor on the member data translates complex member data into consumable data that organization advocates have at their fingertips when interacting with a member. In various embodiments, for example the system and method of the disclosure implemented in a healthcare association context, the analytics described herein enable the aggregation of several types of data, e.g., healthcare claims history data, demographics data, healthcare expenses data, behavioral data, geographic data, provider availability data, and the like.

A further aspect of the present disclosure provides a holistic GUI presented to the advocate. Information displayed in the GUI, including the reason for the member's call, allows the advocate to quickly address the member's needs and offer suggestions to the member, e.g., in a healthcare association context, opportunities for the member to improve their use of the healthcare industry, opportunities for saving money, and programs that may help the member improve their health and well-being.

The disclosed intelligent routing techniques streamline and simplify inbound communication from members of an organization such as healthcare plan members. The disclosed intelligent routing techniques use several data points to connect the member with an organization advocate most appropriately suited to address the member's concerns. The disclosed systems and methods provide improvements over present technologies by utilizing an improved conversation management processor, within a highly secure networked computing environment(s), that applies specific, tailored rules/logic to data from multiple sources.

BRIEF DESCRIPTION OF THE DRAWINGS

Embodiments of devices, systems, and methods are illustrated in the figures of the accompanying drawings, which are meant to be exemplary and non-limiting, in which like references are intended to refer to like or corresponding parts, and in which.

DETAILED DESCRIPTION

Figure 1:
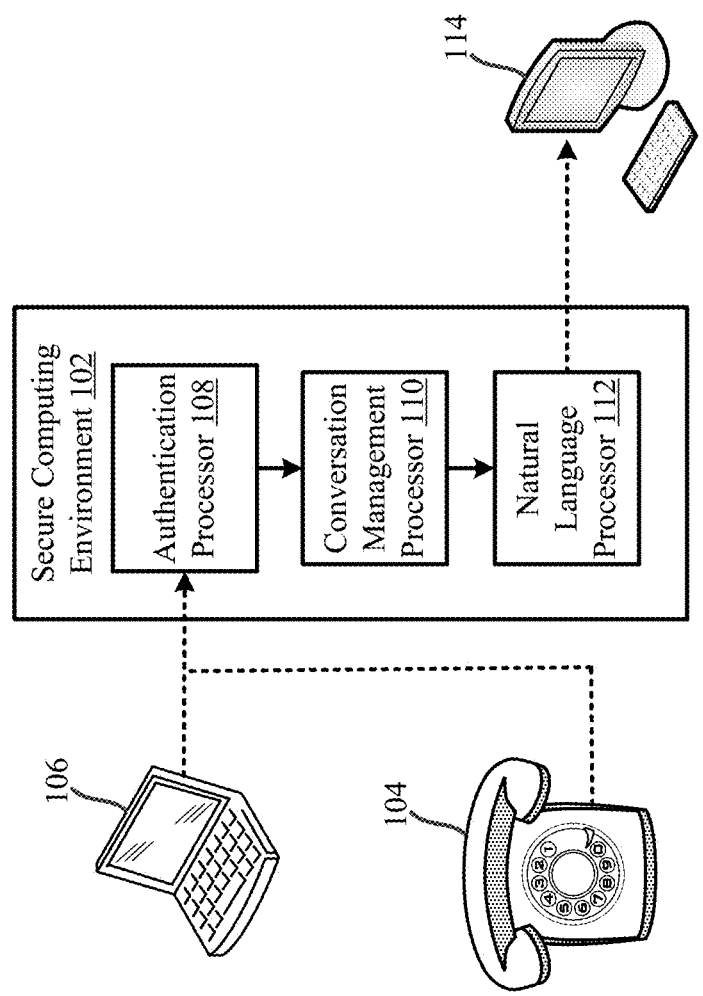
FIG. 1 is an overview system diagram illustrating a system for implementing intelligent routing according to the disclosure.

The detailed description of the present disclosure set forth herein makes reference to the accompanying drawings, which show various embodiments by way of illustration. While these various embodiments are described in sufficient detail to enable those skilled in the art to practice the disclosure, it should be understood that other embodiments may be realized and that logical and physical changes may be made without departing from the spirit and scope of the disclosure. Thus, the detailed description herein is presented for purposes of illustration only and not of limitation. For example, the steps recited in any of the method or process descriptions may be executed in an order other than as presented and are not limited to the order presented. Moreover, references to a singular embodiment may include plural embodiments, and references to more than one component may include a singular embodiment.

The present disclosure provides a network including components for intelligent routing and extensive and specialized processes for transforming vast amounts of data, in the illustrative embodiment healthcare data, into consumable data, i.e., member and household level data, used for intelligently routing members to appropriate organization advocates within a network of interconnected computing devices. Since healthcare data, which is highly sensitive and personal, is involved in multiple embodiments disclosed herein, one skilled in the art should appreciate that the data processing and intelligent routing of the present disclosure occur in a highly secure, networked computing environment. While the illustrative embodiments described herein may relate to healthcare information, it should be appreciated that secure systems as described may be implemented according to the disclosure for intelligent routing and transformation of other types of sensitive information such as financial information, legal information, national security information, or the like. The sophisticated, specialized, and specially configured networked computing environment and processes described herein, for example, facilitate the intelligent routing of a member with access to a network to a single organization advocate within the network capable of handling all, or nearly all, of the member's needs.

The present disclosure gives members of an organization a single point-of-contact within an optimized, secure network to address all their needs as provided for by an advocate accessible through a computing device within the network. The predictive personalization and intelligent routing configuration(s) described herein streamlines and simplifies inbound communication from members of an organization. The predictive personalization and intelligent routing configuration(s) use several data points to connect the member with an advocate who can most appropriately address the member's concerns. Illustrative data points, in a healthcare implementation, used in determining routing include demographic data, recent medical or pharmacy claims data, clinical program enrollments and/or opportunities data, current health state data, incentive opportunities data, health risk assessment results data, and the like. The herein disclosed systems and methods provide improvements over present technical environments by using an intelligent conversation management processor and specially configured data sources to more precisely route calls to appropriate advocates within the network. The intelligent routing described herein is not limited to typical channels of service, e.g., telephone. Rather, the intelligent routing may be applied to various channels of communication such as instant messaging and email, for example.

Referring to FIG. 1, an overview diagram illustrating a system for intelligently routing a call or communication from a member of an organization to an appropriate advocate connected for communication within the network is described. The system includes a secure computing environment or network 102. Various embodiments described herein involve sensitive and/or personal information. Thus, it should be appreciated that the secure computing environment 102 is not a general purpose computing environment. Rather, the secure computing environment 102 implements specially configured security parameters, and may be part of a highly secure network of multiple secure computing environments.

A member contacts the secure computing environment 102 via a telephone 104 or a computing device 106. The member's communication is first directed to an authentication processor 108, which authenticates the member with a member file (in storage within the secure computing environment 102). For example, the authentication processor 108 may perform automatic number identification (ANI) processes to obtain caller ID data that can be referenced against caller ID data contained within member files within the secure computing environment 102. It should be appreciated, however, that authentication techniques other than ANI may be implemented in accordance with the present disclosure.

Once authenticated, the member's information/data is processed using specific rules of a conversation management processor 110. The conversation management processor 110, generally determines an implicit or anticipated level of call messaging presentation and advocate support most appropriate for the member. This is also referred to herein as intelligent routing of the member, and is described in greater detail hereinafter. For example, the conversation management processor 110 may label the member's need as basic, complex, or clinical in nature.

A natural language processor 112 analyzes the spoken words of the member to isolate the member's expressed or explicit need. Once processing by the conversation management processor 110 and natural language processor 112 is complete, the member call or communication link is routed to an appropriate advocate's terminal (e.g. call center terminal) of the organization and the member's file with appropriate data as determined based on rules, e.g. processed by the conversation management processor 110, is transmitted to the advocate's device 114.

Figure 2:
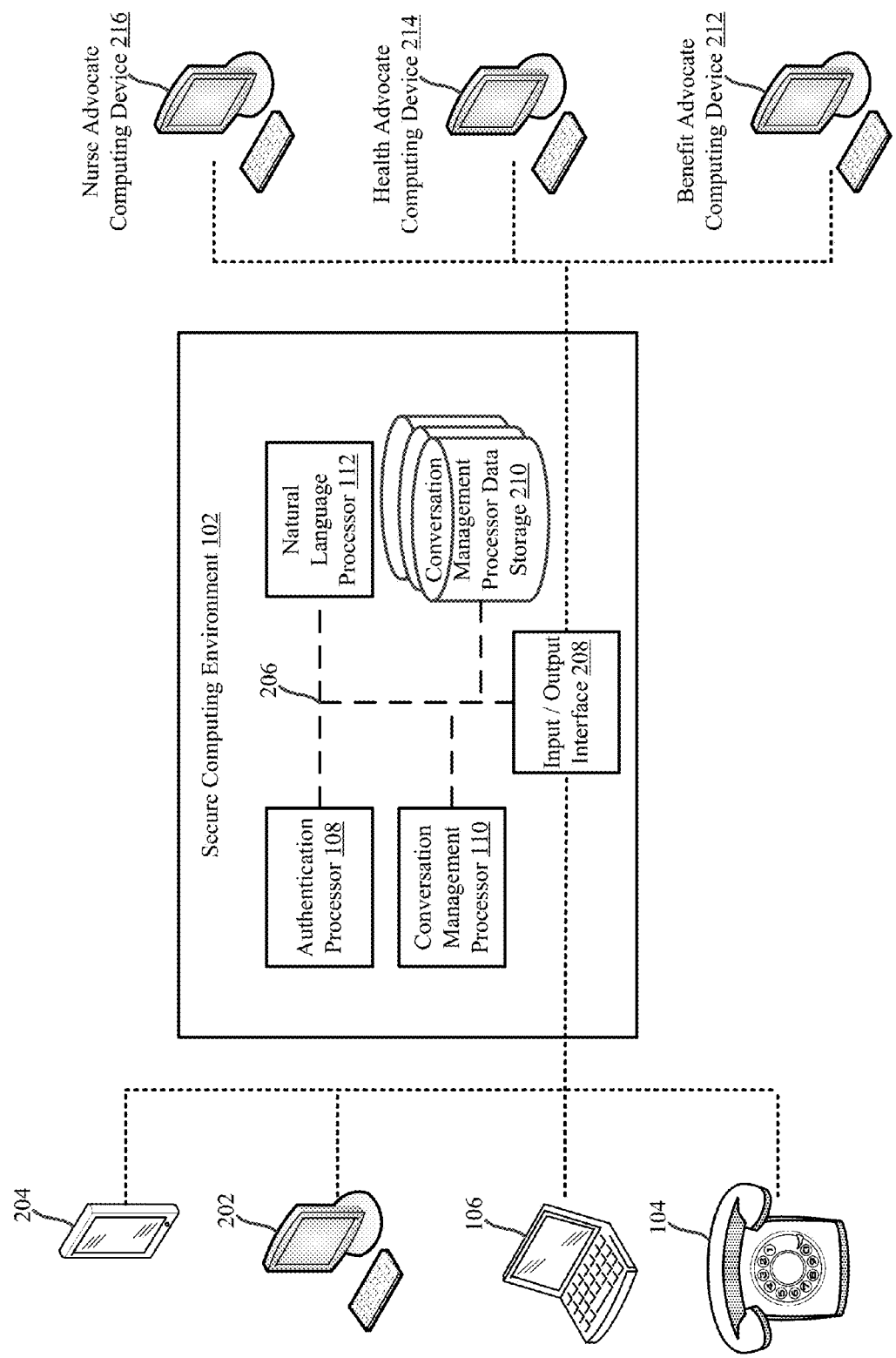
FIG. 2 is a detailed system diagram illustrating implementation of intelligent routing of a member of an organization to an appropriate organization advocate within a communication network.

Referring now to FIG. 2, the system of FIG. 1 for intelligent routing of a member of an organization connecting to the network, to an appropriate advocate within the secure network is described in greater detail. A member may interact with the secure computing environment 102 using various technologies, e.g., audibly via the telephone 104, or electronically using the laptop 106, a desktop computer 202, or via an application on a smart device 204. The smart device 204 may be a smart phone, tablet, or other like device that implements software in the form of software applications.

The components of the secure computing environment 102 may be connected via one or more buss(es) 206. In addition, various components of the secure computing environment 102 may be connected through direct linkages. The secure computing environment 102 includes an input/output interface 208 that enables the secure computing environment 102 to communicate data, control signals, data requests, and other information with other devices including computers, data sources, storage devices, and the like. The input/output interface 208 may be configured to communicate via wired or wireless connections. One skilled in the art should appreciate that the secure computing environment 102 may receive audio, image, text, video, and other inputs and transmit tailored user interface (UI) data to another computer or other source via the input/output interface 208.

When the member communicates with the secure computing environment 102, the member's communication is directed from the input/output interface 208 to the authentication processor 108. The authentication processor 108 determines the identity of the member, for example as described herein above with respect to FIG. 1. When a new member of the organization contacts the secure computing environment 102, the authentication processor 108 may not recognize the member's communication source, e.g., telephone 104, computer 106, 202, or smart device 204. When this occurs, the member may be requested to provide additional information, for example their member ID and/or date of birth (DOB) for authentication purposes. When the member subsequently contacts the secure computing environment 102, the authentication processor 108 uses, for example, ANI to automatically identify the member. For example, if the member uses the telephone 104, the authentication processor 108 is configured to identify the member based on the telephone number.

The secure computing environment 102 also includes the conversation management processor 110 and the natural language processor 112 as described herein. The natural language processor 112, while being configured to analyze the spoken words of a member, may also be configured to analyze the typed text of a member. If the member uses audible means of the telephone 104, computer devices 106, 202, or smart device 204, the natural language processor 112 directs simple, open-ended questions to the member and analyzes the member's responses to determine the member's explicit need(s). Use of the natural language processor 112 is beneficial because it eliminates the necessity of complicated phone trees.

The secure computing environment 102 further includes conversation management data storage 210. The conversation management data storage 210 houses data processed and/or generated by the conversation management processor 110 as described herein. In an illustrative embodiment, the present disclosure may be implemented within the healthcare industry. In this embodiment, the secure computing environment 102 may include several specially configured data stores such as, for example, a pharmacy claims storage, a program consumption storage, a medical claims storage, a screening results storage, an attitudinal data storage, a provider availability storage, a geographic data storage, a demographic data storage, and a cost of care storage. The aforementioned data stores may be implemented as stand-alone data stores within the secure computing environment 102, or they may be subcomponents of the conversation management data storage 210. One skilled in the art should appreciate that additional stores of data may be implemented as a function of the organization, network and services/products provided.

Upon the specific processes performed by the conversation management processor 110 being performed, and upon the member's explicit need(s) being ascertained by the natural language processor 112, the member connection is routed to an organization advocate within the network and the member's file is transmitted to the advocate's device. The advocate should be a person competent to handle most if not all of the member's needs. The organization's advocates may be segregated into tiers based on complexity of issues. For example, in a healthcare industry embodiment, the organization may have a Tier 1 benefit associate (illustrated as 212), a Tier 2 health advocate (illustrated as 214), and a Tier 3 nurse advocate (illustrated as 216). For example, the benefit advocate 212 may be a competent advocate when the member has infrequent health issues, i.e., the member is in good health and mainly needs routine/preventative care. The health advocate 214 may be a competent advocate when the member has complex claim issues, i.e., the member frequently contacts the secure computing environment 102 or is an out-of-network individual. The nurse advocate 216 may be a competent advocate when the member has significant health issues, i.e., the member has chronic, complex health issues.

Figure 3:
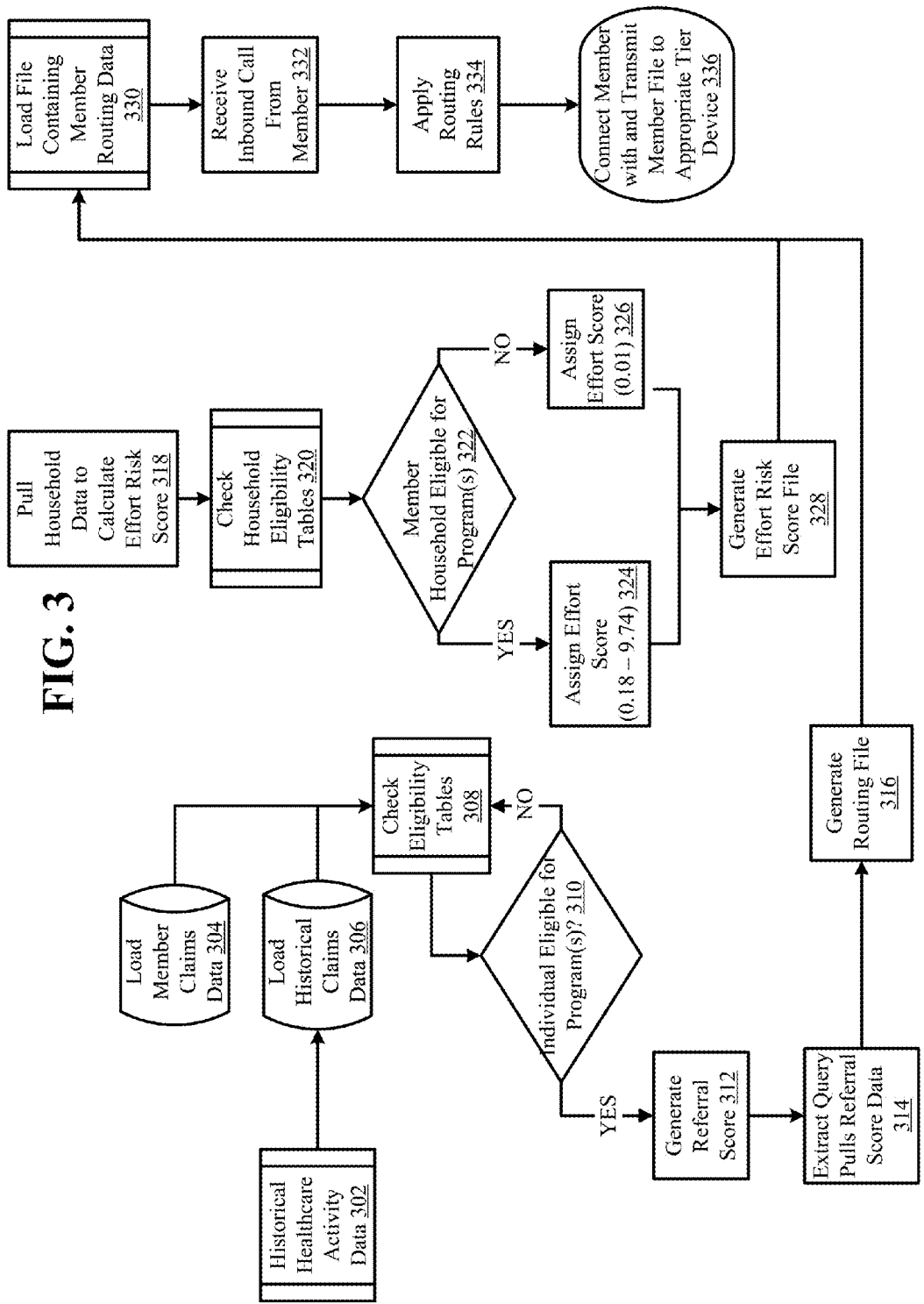
FIG. 3 is a process flow diagram illustrating a method for intelligent routing of a member of an organization to an appropriate organization advocate within a communication network.

Attention is now given to FIG. 3, which illustrates an overview of processing for intelligent routing a member connection and its account file to an appropriately tiered advocate and its computing device. In a health care embodiment context, when an individual becomes a member of the organization, historical healthcare activity data of the member is obtained (illustrated as 302) to be maintained or accessible to the secure network 102. The historical healthcare activity data may include medical claims data, pharmacy claims data, biometrics results data, and demographic data, for example. In an example, the member may provide the historical activity to the secure computing environment 102 via a user interface of a computing device 106, 202, 204. Alternatively, for example, the member may provide the secure computing environment 102 authorization to obtain historical healthcare activity data from various sources, e.g., hospital computing environments, doctors office computing environments, and the like. The secure computing environment 102 may actively retrieve or passively obtain the historical healthcare activity data from the various sources on a periodic basis, e.g., weekly, daily, etc. The received historical healthcare activity data is stored within the various data stores of the secure computing environment 102, as illustrated in FIG. 2.

Various healthcare data of the member is loaded by the secure computing environment 102. Both post-membership enrollment claims data and pre-membership historical claims data are loaded (illustrated as 304 and 306 respectively). Post-enrollment claims data of a member may be stored, i.e., refreshed, into the secure computing environment 102 on a periodic basis, e.g., weekly, daily, hourly, etc. Thereafter, program eligibility tables are checked against the loaded claims data (illustrated as 308). The tables may be in structured query language (SQL) format. The eligibility tables contain eligibility requirements for various programs offered by the organization that operates and maintains the secure computing environment 102. The secure computing environment 102 may check the member's claims data against the eligibility tables on a periodic basis, e.g., monthly, weekly, daily, etc.

By checking the member's claims data (both historical and post-enrollment) against the program requirements within the eligibility tables, the member's program elibility(ies) is determined (illustrated as 310). If the member's claims data does not satisfy a single program's eligibility requirements, the eligibility tables are re-checked (illustrated as 308). Re-checking of the eligibility tables may occur on a periodic basis, such as monthly, weekly, daily, etc. Alternatively, if the member's claims data satisfies at least one program's eligibility requirements, a referral score(s) for the member is generated (illustrated as 312). If the claims data satisfies more than one program's requirements, a referral score may be generated for each eligible program. However, one skilled in the art should also appreciate that a single referral score may be generated for multiple eligible programs.

In a healthcare context, a referral score may be equated to the propensity of the member to contact the organization regarding the eligible program. Each referral score is derived from multiple variables, such as pharmacy first fill data, treatment decision support (TDS) program referral data, a pharmacy value factor score, an impact pro cost risk score, a monetized value, a household opportunity value, comprehensive medication review (CMR) program data, and a cost risk score, for example. The cost risk score may be based on claims data, and optionally additionally based on a service index score.

The decision whether to route a member and its account file to a Tier 3 nurse advocate and its device 230 may be based on the member's referral score across multiple domains. For example, if the member's referral score surpasses a single requisite threshold, the member connection and its account file may be routed to the Tier 3 nurse advocate and its device 230. The referral score(s) of a member may determine spend risks associated with the member. This may be based on the member's healthcare utilization data. Referral score data of the member is pulled using extract queries (illustrated as 314) and a routing file for the member is generated (illustrated as 316).

The member's household healthcare activity data is pulled to calculate an effort risk score (illustrated as 318). The member's household data may include medical claims data, pharmacy claims data, biometrics results data, and demographic data, for example, for each individual in the member's household. Household program eligibility tables are thereafter checked (illustrated as 320). The household tables may be in structured query language (SQL) format. The household eligibility tables may contain eligibility requirements for various household level programs offered by the organization that operates and maintains the secure computing environment 102. Thus, the member household data checked against the household eligibility tables includes data corresponding to various individuals within the member's household. For example, the household eligibility tables may be checked on a periodic basis, e.g., monthly, weekly, daily, etc.

It is then determined whether the member's household, i.e., household healthcare activity data, satisfies any of the program eligibility requirements (illustrated as 322). Regardless of the determination, the member's record/account file is assigned an effort risk score. An effort risk score is based on a variety of independent variables, such as diagnosis data, demographics data, and outstanding claims data, for example. In a general sense, an effort risk score demonstrates the propensity of the member to call the organization. An effort risk score may be based on most frequently occurring diagnosis categories for the member's household. If the household healthcare activity data satisfies at least one program's eligibility requirements, the member's record is assigned an effort risk score of 0.18 to 9.74 (illustrated as 324). If, instead, the member's household healthcare activity data does not satisfy the eligibility requirements of a single program, the member's record is assigned an effort risk score of about 0.01 (illustrated as 326). Assignment of an 0.01 effort risk score may result in the member and its account file being routed to a Tier 1 benefit advocate and its device 226 when the member contacts the organization. An effort risk file is thereafter generated for the member's account file (illustrated as 328).

The member's routing and effort risk files are loaded by the secure computing environment 102 (illustrated as 330). When this occurs, the member's routing data is analyzed to differentiate whether the member is a new or existing member. If the member is an existing member, the member's account file is refreshed with the newly generated referral and effort risk score values. If, on the other hand, the member is a new member, an account file with the newly generated referral and effort risk score values is created for the member. When the member contacts the organization, the member is identified by the authentication processor 108 as described herein above (illustrated as 332). After authentication occurs, the conversation management processor 110 applies intelligent routing rules to the member's account file to determine which advocate Tier to transmit the member connection and its account file to (illustrated as 334). Various routing rules described herein below are used. Once the appropriate Tier is identified, the member is connected with and the member's account file is transferred to the appropriate tiered advocate and its device (illustrated as 336).

Figure 4A:
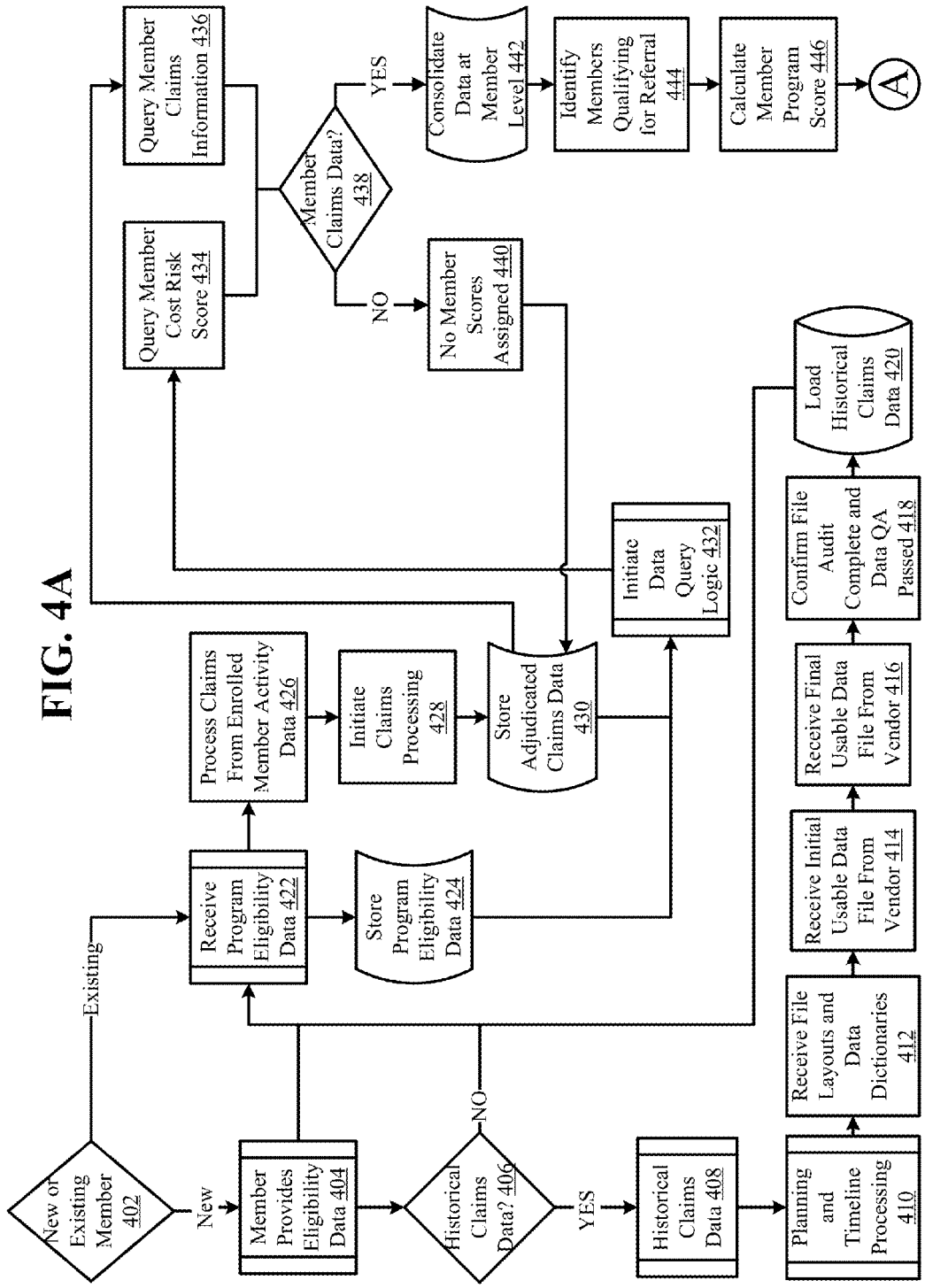
FIGS. 4A through 4C are process flow diagrams illustrating a method for intelligent routing of a member of an organization to an appropriate organization advocate within a communication network.
Figure 4B:
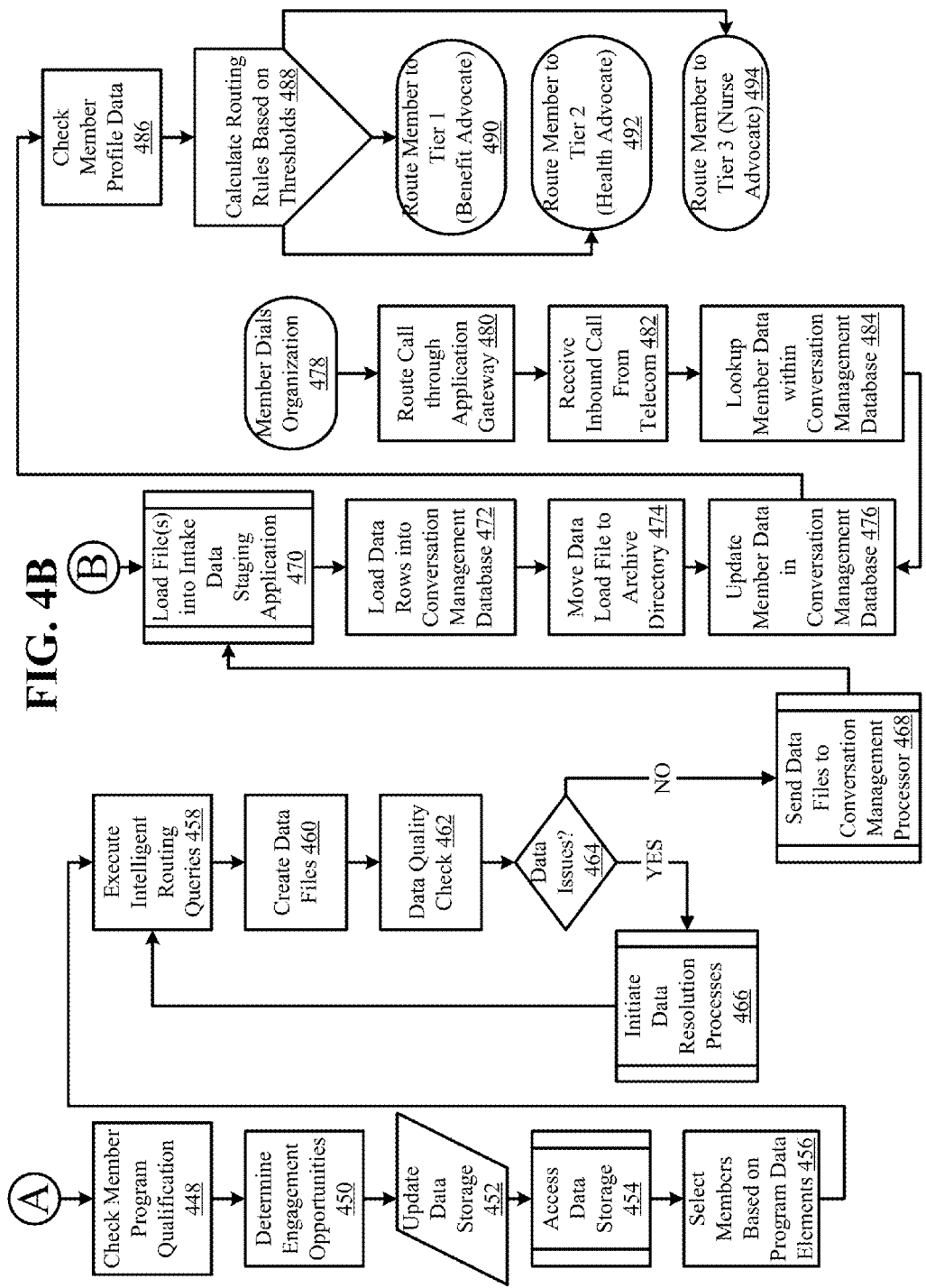
Figure 4C:
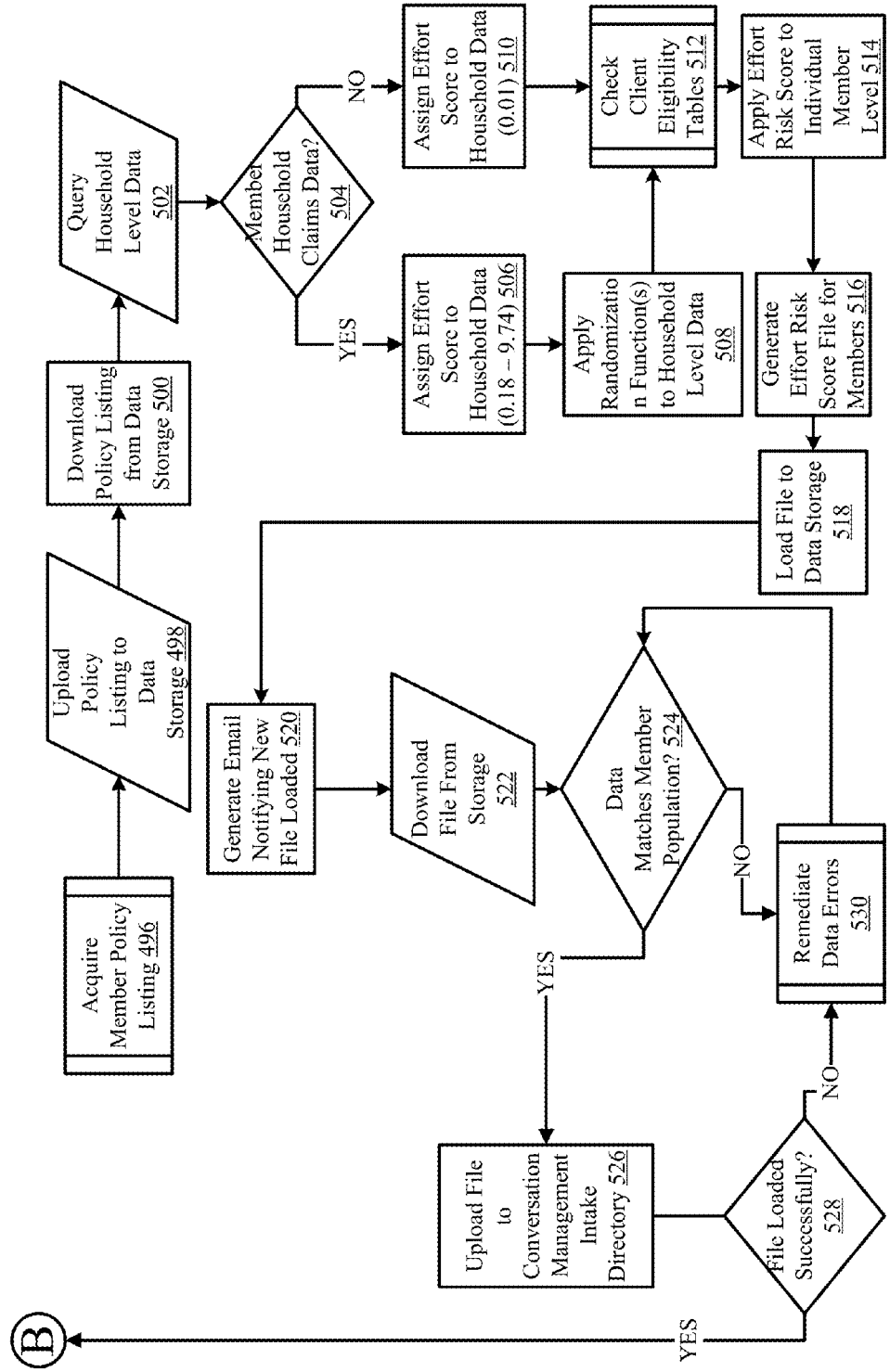

FIGS. 4A through 4C illustrate a method for intelligent routing of a connection of an organization's member and its account file to an appropriately tiered advocate and its computing device within the network. Referring specifically to FIG. 4A, it is determined whether the member is a new or existing member of the organization (illustrated as 402). This may entail the authentication processor 108 determining whether the member has an account file within the secure computing environment 102 and the comprehensiveness of any such account file. For example, a new member's account file may not contain historical healthcare claims data corresponding to claims made by the member prior to enrollment within the organization. Additionally, this may also entail the authentication processor 108 comparing demographic data provided by the member to demographic data stored within the secure computing environment 102.

If the member is new, the member may provide data demonstrating that they are eligible for one or more programs of the organization (illustrated as 404). This may involve the secure computing environment 102 providing the member, via a device, program eligibility requirements. Also, if the member is new, it is determined whether historical healthcare claims data will be provided to the secure computing environment 102 (illustrated as 406). Members may have the discretion of whether external, pre-membership claims data will be submitted upon enrollment with the organization.

If the member desires that external, pre-membership claims data be provided, such data is received by the secure computing environment 102 (illustrated as 408). In an example, the new member provides historical claims data to the secure computing environment 102 via a user interface of a computing device 106, 202, 204. Alternatively, for example, the new member may provide the secure computing environment 102 authorization to obtain healthcare claims data from various computing sources. Planning and timeline review processing of the historical claims data may be performed upon receipt of the data by the secure computing environment 102 (illustrated as 410).

The secure computing environment 102 may receive file layouts and data dictionaries for the historical claims data (illustrated as 412). Optionally, the secure computing environment 102 may receive an initial usable data file from the data source/vendor of the historical claims data (illustrated as 414). Thereafter, a final usable data file is received from the historical claims data source/vendor (illustrated as 416). It is then confirmed that the file audit process has been completed and that the data passed organization quality assurance standards (illustrated as 418). The organization may desire that step 418 be performed within a certain amount of days, e.g., 10, after receipt of the data. The member's historical claims data is then loaded into one or more storages of the secure computing environment 102 (illustrated as 420).

If the member is determined to be an existing member at step 402, if the member provides eligibility data at step 404, if historical claims data is not to be presented at step 406, or if the historical claims data is loaded at step 420, the secure computing environment 102 receives member program eligibility data (illustrated as 422). Upon receipt, the secure computing environment 102 stores the eligibility data (illustrated as 424) and/or processes claims from the enrolled member activity data (illustrated as 426). The enrolled member activity data may be received via a claims highway from healthcare providers. If the enrolled member activity data is to be processor at step 426, the secure computing environment 102 directs a relevant processor, e.g., the conversation management processor 110, to initiate claims processes (illustrated as 428). Claims processing is thereafter performed (not illustrated) and adjudicated claims data is stored (illustrated as 430).

Once the program eligibility data is stored at step 424, the secure computing environment 102 initiates data query logic (illustrated as 432). The logic/rules allow for data to be pulled from multiple sources, thereby enabling the secure computing environment 102 to act as a data repository for multiple systems to access. When steps 430 and 432 are complete, the member's cost risk score and claims information is queried (illustrated as 434 and 436 respectively). A cost risk score is applied to every member of the organization. At step 436, various information such as, for example, pharmacy data, medical claim data, and lab results data is queried for members of the organization.

It is then determined whether claims data exists for each of the organization's members (illustrated as 438). If no data exists for a member, no member score is assigned for the member (illustrated as 440) and the member's data is stored with the adjudicated claims data (illustrated as 430). Alternatively, if it is determined that claims data exists for various organization members, the claims data is consolidated on a member level (illustrated as 442) and members qualifying for a referral are identified (illustrated as 444). The referral determination of step 444 is performed on the member level, not the cumulative member household level. A member identified as qualifying for a referral is assigned a unique ID different from the member's member ID.

A program score for each member qualifying for a referral is thereafter calculated (illustrated as 446). Each program score relates to future spend risks based on member healthcare utilization data. Examples of healthcare utilization data include, for example, cost risk score, pharmacy first fill data, TDS program referral data, a pharmacy value factor score, a cost risk score, a monetized value, a household opportunity value, and CMR program data.

Referring to FIG. 4B, member program qualification is checked (illustrated as 448). This may involve the secure computing environment 102 reviewing member scores and program referral identifications to determine whether a member qualifies for a referral based on, for example, member opt out preferences, suppression logic, i.e., referral attempt thresholds, or member program enrollment, i.e., the member is already enrolled or has already participated in the program. Additionally, the secure computing environment 102 may determine member program qualification at step 448 based on program co-management rules, conflicting program rules, and hierarchy of program impact rules, for example.

The secure computing environment 102 also determines engagement opportunities (illustrated as 450). Engagement opportunities relate to qualified programs of members. For example, a low risk member may receive mail campaigns; a medium risk member may receive email and mail campaigns; and a high risk member may receive unsolicited, proactive organization outreach calls, as well as phone, email, and mail campaigns. Thereafter, a data storage containing program qualification/referral information and engagement opportunities information is updated (illustrated as 452).

The data storage containing the program qualification/referral information and engagement opportunities information is accessed (illustrated as 454) to extract data, and members are selected based on program data elements (illustrated as 456). For example, analyzed program data elements include pharmacy first fill data, value factor score, TDS program referral data, cost risk score, monetized value, household opportunity value, nurse monetized value, and CMR program data. Thereafter, the secure computing environment 102 instructs one or more processors therein to execute intelligent routing queries (illustrated as 458). An example processor includes the conversation management processor 110 described herein above. The intelligent routing queries are executed to extract data from the data storage of step 454. Extracted member specific data may be aggregated to household level data by the processor(s).

Once the household level data is generated, a file for the data of each household is created (illustrated as 460). The created files are full replace files, i.e., they replace any temporary household files generated at step 458. For example, the data of a household may be represented in two files: a routing logic file and a nurse monetized value file. A data quality check is performed on the household level files (illustrated as 462). Validation quality checks may be performed to compare counts, thereby ensuring populations of members have been successfully identified as qualifying for a referral(s).

After the quality check is performed, it is determined whether there are any data issues (illustrated as 464). If there are outstanding data issues, data resolution processes are initiated (illustrated as 466) and the secure computing environment 102 re-instructs a processor(s) to execute intelligent routing queries (illustrated as 458). Conversely, if no outstanding data issues remain, the household level data files are transmitted for processing by the conversation management processor 110 (illustrated as 468).

The conversation management processor 110 loads the household level files into an intake data staging application of the secure computing environment 102 (illustrated as 470). The data staging application receives files and prepares the files for loading into the conversation management processor data storage 210 of the secure computing environment 102. Preparation of the files may take seconds, minutes, hours, days, etc. depending upon implementation and the vastness of the files. Data rows are loaded into the conversation management processor data storage 210 (illustrated as 472). Each data row may be specific to a single household level file. Data load files are thereafter moved to an archive directory (illustrated as 474) and member data is updated in the conversation management processor data storage 210 (illustrated as 476). Once files have successfully updated member rows in the conversation management processor data storage 210, the conversation management processor 110 may properly interact with the household level files. For example, the conversation management processor 110 may properly route calls, perform dynamic prompting interactive voice response (IVR) member interaction, and provide screen popups and virtual call center desktops to advocate devices. Alternatively, the IVR member interaction may be performed by the natural language processor 112.

When a member calls/dials the organization (illustrated as 478), the call is routed through an application gateway request (illustrated as 480). At the application gateway, validation is performed to indicate whether the call should be directed through the conversation management processor 110 for appropriate call routing. This validation may be performed by the authentication processor 108. The call is thereafter received by the conversation management processor 110 (illustrated as 482) and data pertaining to the calling member is looked up in the conversation management processor data storage 210 (illustrated as 484). If any new member data is available, the member's data in the conversation management processor data storage 210 is updated (illustrated as 476).

After the conversation management data storage 210 is updated, the member's profile data is checked (illustrated as 486). The member's profile is validated/checked by the conversation management processor 110 using extension tables, which house member household routing data. All members of the organization can route to an advocate tier if member scores meet certain requirements described herein. The conversation management processor 110 then calculates routing rules based on thresholds (illustrated as 488). For example, based on values of tier routing values, the conversation management processor 110 may compare values to determine tier routing. The comparisons may include value thresholds as an "if/then" format. Default routing causes the member to be routed to a Tier 1 advocate (illustrated as 490).

Default routing occurs when the member's household does not have any data or the member's household data does not surpass any of the thresholds described with respect to steps 492 and 494 below. The member is routed to a Tier 2 advocate (1) if their effort risk score is greater than XX or (2) the member's monetized value is between YY and ZZ (illustrated as 492). The XX threshold is determined by using a ranking algorithm that assigns an effort risk value to a diagnosis. For example, if the household had the diagnosis that is listed on their claim in the past 30 days, it is assigned a value. The YY and ZZ thresholds are determined using subject matter expert knowledge and qualitative research to determine the dollar amount that is considered high value to the payor. The value may be derived based on typical costs of clinical treatments and assigned by the consumer or clinical nurse. Moreover, the member is routed to a Tier 3 advocate (1) if their monetized value is greater than X, (2) if the member's cost risk score is greater than or equal to Y, (3) if the member's pharmacy first fill equals "yes" (i.e., the member filled a new prescription for the first time in the past 30 days), or (4) if the member's pharmacy value factor is greater than or equal to Z and the member's CMR program data equals "yes" (i.e., yes is assigned when a member is filling multiple prescriptions and there is a likelihood that there are alternative prescriptions or potential drug interactions and the intervention of a pharmacist is required) (illustrated as 494). The X threshold is determined using subject matter expert knowledge and qualitative research to determine the dollar amount that is considered high value to both the member and organization. The value may be derived based on typical costs of clinical treatments and assigned by the consumer or clinical nurse. The level of Y is determined using subject matter expert knowledge and qualitative research to determine the dollar amount that is considered high cost to the payor. The value may be derived based on typical costs of clinical treatments and assigned by a quantitative algorithm within the health insurance organization. The Z threshold is determined based on the risk of having medication issues where pharmacist intervention is required and is calculated using an algorithm derived from historical data. As described, the thresholds of Tier 2 and Tier 3 routing are implemented as "OR" functions. However, one skilled in the art should appreciate that the Tier 2 and Tier 3 thresholds may be implemented as "AND" functions without departing from the present disclosure.

Referring specifically to FIG. 4C, the member's policy listing is acquired (illustrated as 496) and the policy listing is uploaded to a data storage of the secure computing environment 102 (illustrated as 498). The uploaded member policy may be added into effort risk score calculations. The policy listing is thereafter downloaded from the data storage (illustrated as 500) and member household level data is queried (illustrated as 502).

Based on the query, it is determined whether household level claims data for the member exists (illustrated as 504). If household level claims data exists, an effort score of 0.18 to 9.74 is assigned to the household data (illustrated as 506), and a randomization function(s) is applied to the member's household level data (illustrated as 508). The effort score may be based on a variety of independent variables, such as diagnosis data, demographics data, and outstanding claims data, for example. The randomization function(s) adjust member data scores evenly across member populations from 7.65 to 7.64 until a staffing call volume threshold, e.g., Tier 2 routing threshold has been satisfied. Conversely, if no member household level data exists, the member's file is assigned a household effort score of 0.01 (illustrated as 510).

After steps 508 and 510 occur, program eligibility tables are checked (illustrated as 512). The household level data may be expanded/transformed into individual member data related to a specific household in order to properly check the eligibility tables in a beneficial and expeditious manner. An effort risk score is then applied to the data on an individual member level (illustrated as 514). The highest frequency effort risk score of the member's household may be applied to the member's individual-level file. When this occurs, all of the individuals of a household receive the same effort risk score. This may result in all of the individuals of a household being intelligently routed the same way by the conversation manager processor 110. An effort risk score file is then generated for each member (illustrated as 516) and the member files are loaded into a data storage of the secure computing environment 102 (illustrated as 518).

An email may then be generated by the secure computing environment notifying an individual of the data file loading (illustrated as 520) and the data files are thereafter downloaded from the data storage (illustrated as 522). Download of the data file(s) may involve performing a query operation specific to policy number. The data file(s) may be summarized at the household level when downloaded. The data is then validated to determine whether the data matches the member population (illustrated as 524).

The data may be validated by comparing the data to count of membership by policy for, for example, missing policies, target population identified, membership policy volume count, and effort risk score distribution, i.e., risk bucket percentage. The validation processes may be performed prior to the data files being transmitted to the conversation management processor 110 and its corresponding data storage 210. Validation may involve verifying policy numbers within the data files and confirming the effort risk distribution of the data. A high effort risk score may be between 12% and 18%. When a data file is validated, the file is uploaded to a conversation management intake directory, e.g. in the conversation management processor data store, (illustrated as 526) and it is determined if the file was loaded successfully (illustrated as 528). File load success may be determined by checking the conversation management data store. A validating file may be in an archive folder of the conversation management data store. If the file load was unsuccessful or if the data was not validated, the data errors are remediated (illustrated as 530) and the data is re-validated (illustrated as 524). If the file was loaded successfully, the file is loaded into an intake data staging application (illustrated as 470).

Figure 5A:
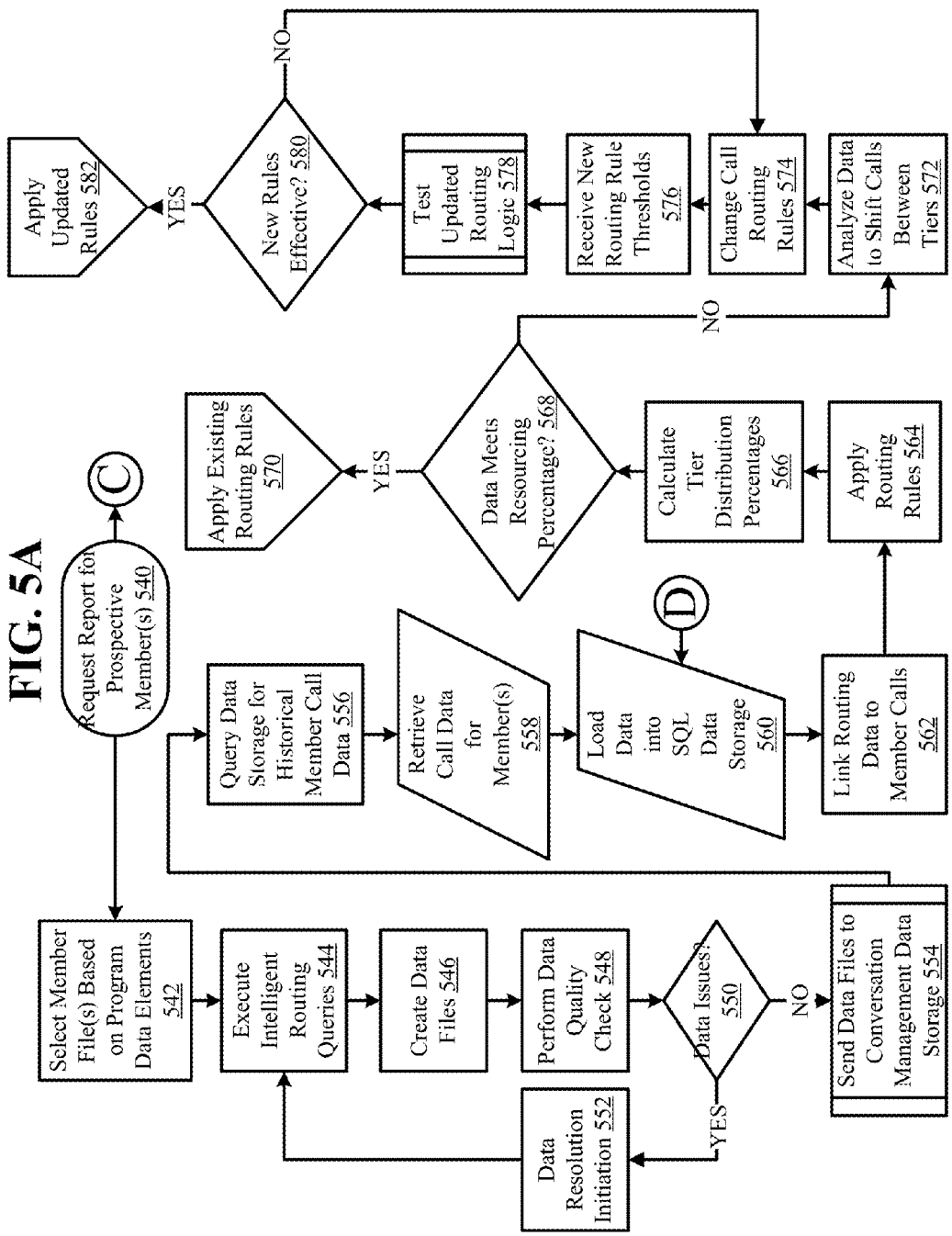
FIGS. 5A and 5B are process flow diagrams illustrating a method for performing a quality check on appropriateness of selected intelligent routing rules for intelligent routing of a member of an organization to an appropriate organization advocate within a communication network according to the disclosure.
Figure 5B:
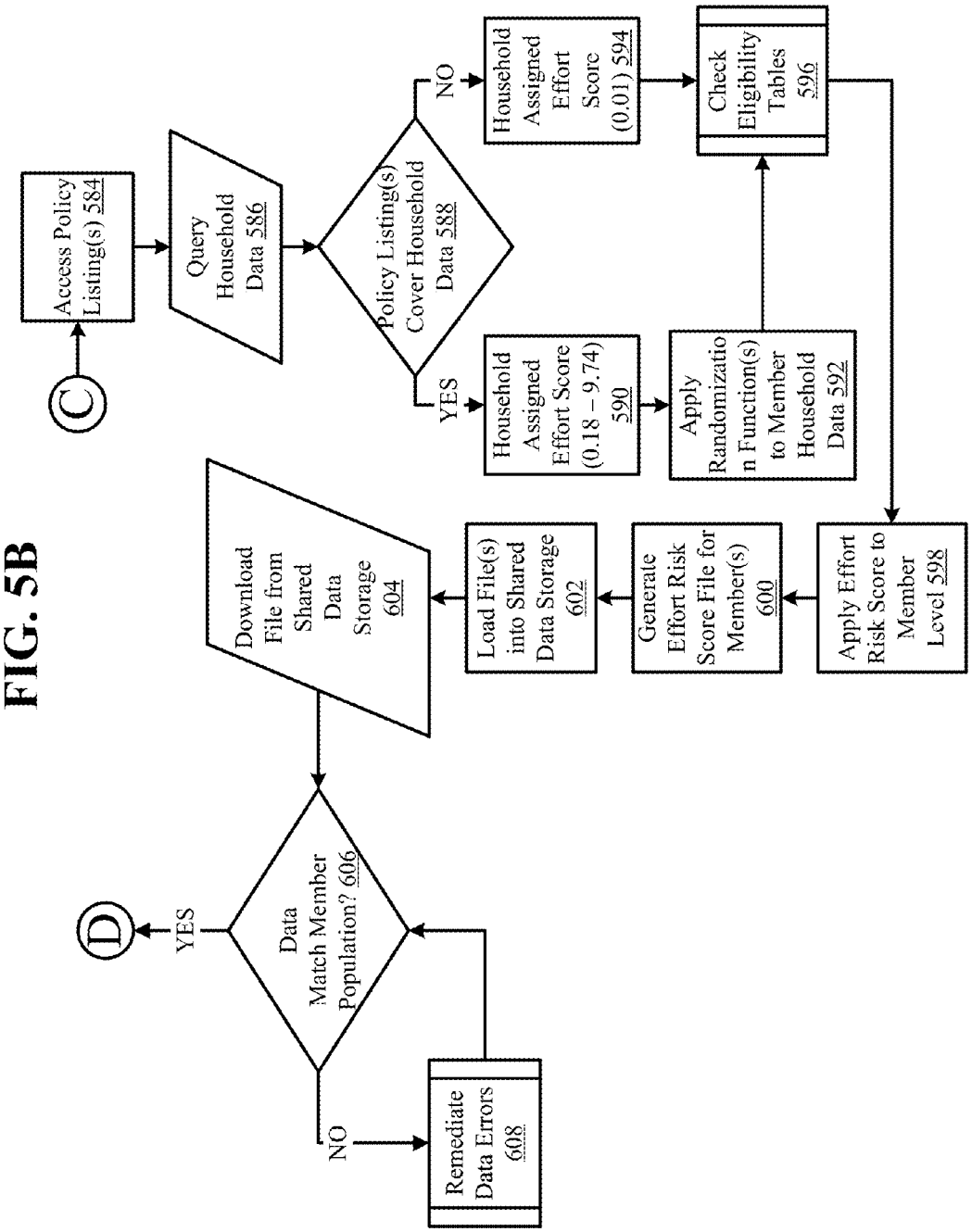

Attention is now given to FIGS. 5A and 5B, which illustrate a method for performing a quality check on the appropriateness of selected intelligent routing rules. As illustrated in FIG. 5A, the method begins with a request for a report for prospective member(s) (illustrated as 540). This may include a request for an ad hoc report, which is a mock up routing file for new onboarding members. In response, a mock routing file is selected based on program data elements (illustrated as 542). The secure computing environment 102 then instructs one or more processors therein to execute intelligent routing queries (illustrated as 544). Data files (either on the member level or household level) are created (illustrated as 546) and a data quality check is performed (illustrated as 548). During the quality check, it is determined whether issues exist within the data (illustrated as 550). If issues are identified, data resolution processes are initiated (illustrated as 552) and, thereafter, intelligent routing queries are re-performed on the data (illustrated as 544). If no issues exist in the data, the mock routing file is transmitted to the conversation management data storage 210 (illustrated as 554). In an example, the conversation management data storage 210 is in a structured query language (SQL) format.

A data storage of the secure computing environment 102 is then queried for historical member call data (illustrated as 556) and historical call data for one or more members is retrieved (illustrated as 558). The retrieved member call data and effort risk score data (sorted by member) are loaded into a specific data storage, such as an SQL data storage, for example (illustrated as 560). The routing data within the SQL data storage is linked to associated member call data also within the SQL data storage (illustrated as 562). For example, linkage of the data may occur at a household level. In another example, data variables that drive intelligent routing, e.g., thresholds and scores, are used to link the routing data to associated household level call data. Linking of the data builds a member specific mock up routing file for further analysis by the secure computing environment 102. The ad hoc report of step 540 is combined with current routing files to analyze rule adjustments for resource allocation routing.

Routing rules as described herein are applied to the linked data (illustrated as 564). Currently configured and implemented routing rules are applied to the member(s) specific mock routing file for analysis of household level call distribution across the tiers of organization advocates. Next, tier distribution percentages are calculated (illustrated as 566) and it is determined whether the present routing rules result in appropriate resourcing percentages/distributions (illustrated as 568). In other words, it is determined whether the routing percentages generated by the present routing rules meet a staffing resource structure of the organization's advocates. For example, appropriate percentages may be defined as 50% of inbound calls being routed to Tier 1 advocates, 30% of inbound calls being routed to Tier 2 advocates, and 20% of inbound calls being routed to Tier 3 advocates. If the percentages are appropriate, the existing, presently implemented routing rules are continually used to intelligently route member's and their account files (illustrated as 570). If, instead, the percentages produced by the presently implemented routing rules are inappropriate, the data is analyzed to shift member calls between advocate tiers in accordance with resourcing requirements (illustrated as 572).

The implemented routing rules are thereafter changed (illustrated as 574) and new routing rule thresholds are received (illustrated as 576). For example, the routing rules may be changed to impact Tier 3 routing with respect to treatment decision support (TDS) and/or cost risk score. Additionally, the routing rules may be changed to impact Tier 2 routing with respect to effort risk score and/or monetized opportunity value. The new/updated routing rules are tested (illustrated as 578) and it is determined whether the new/updated routing rules are effective/appropriate, i.e., generate proper tier distribution percentages (illustrated as 580). Testing of the new routing rules may be performed using an testing application executed by the conversation manager processor 110. If the new routing rules/logic are inappropriate, the routing rules are changed again (illustrated as 574). To the contrary, if the routing rules/logic are effective/appropriate, the new routing rules are thereafter applied to intelligently route member's calls and the member's profile account (illustrated as 582).

As illustrated in FIG. 5B, in response to the report for prospective member(s) being requested at step 540, policy listing(s) are accessed (illustrated as 584) and a query is run on the household level data to extract it from storage (illustrated as 586). It is then determined whether the policy(ies) cover any of the household data (illustrated as 588). If a household is covered by the policy, an effort score of 0.18 to 9.74 is assigned to the household data (illustrated as 590), and a randomization function(s) is thereafter applied to the household data (illustrated as 592). The randomization function(s) adjust household scores evenly across household populations from 7.65 to 7.64 until a staffing call volume threshold, e.g., Tier 2 routing threshold has been satisfied. To the contrary, if a household is not covered by the policy, an effort score of 0.01 is assigned to the household data (illustrated as 594). After steps 592 and 594 are performed, program eligibility tables are checked (illustrated as 596).

Effort risk scores are then applied at the member level of the household data (illustrated as 598) and an effort risk score file for each member is generated (illustrated as 600). The member file(s) is loaded into a shared data storage, e.g. the conversation management processor data store. The stored member file(s) is thereafter downloaded from the shared data storage (illustrated as 604) and it is determined whether the downloaded data file(s) matches member population data (illustrated as 606). Step 606 may involve comparing data elements in the member file to data elements of population data, thereby often aligning and matching member identification number data stored in each file. If the data does not match the member population, the data errors are remediated (illustrated as 608) and the data is reprocessed for conformity with the member population (illustrated as 606). If, however, the data matches the member population, the data is loaded into the SQL data storage (illustrated as 560).

Figure 6A:
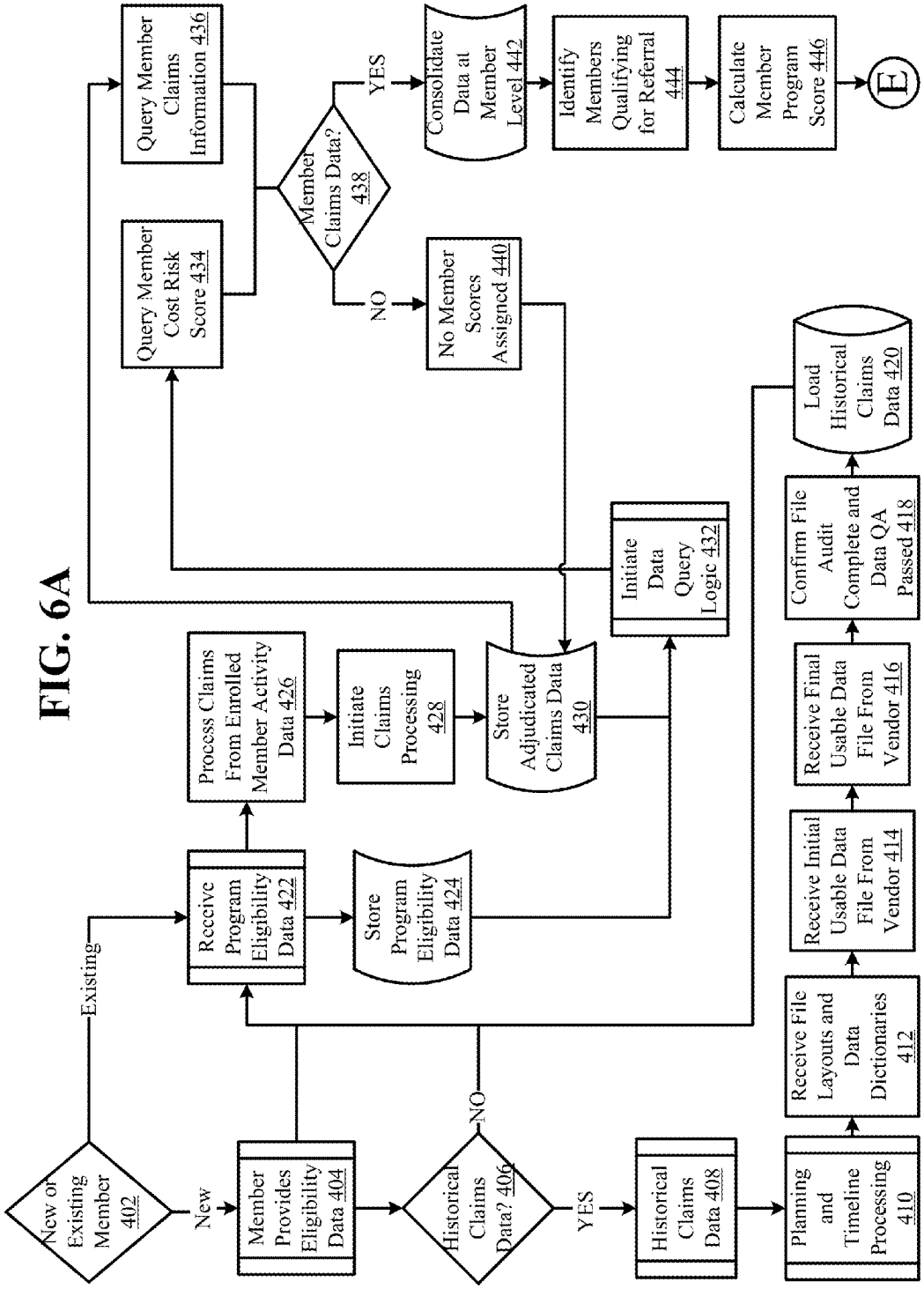
FIGS. 6A through 6C are process flow diagrams illustrating a further embodiment of the method of FIGS. 4A through 4C, for intelligent routing of a member of an organization to an appropriate organization advocate within a communication network.
Figure 6B:
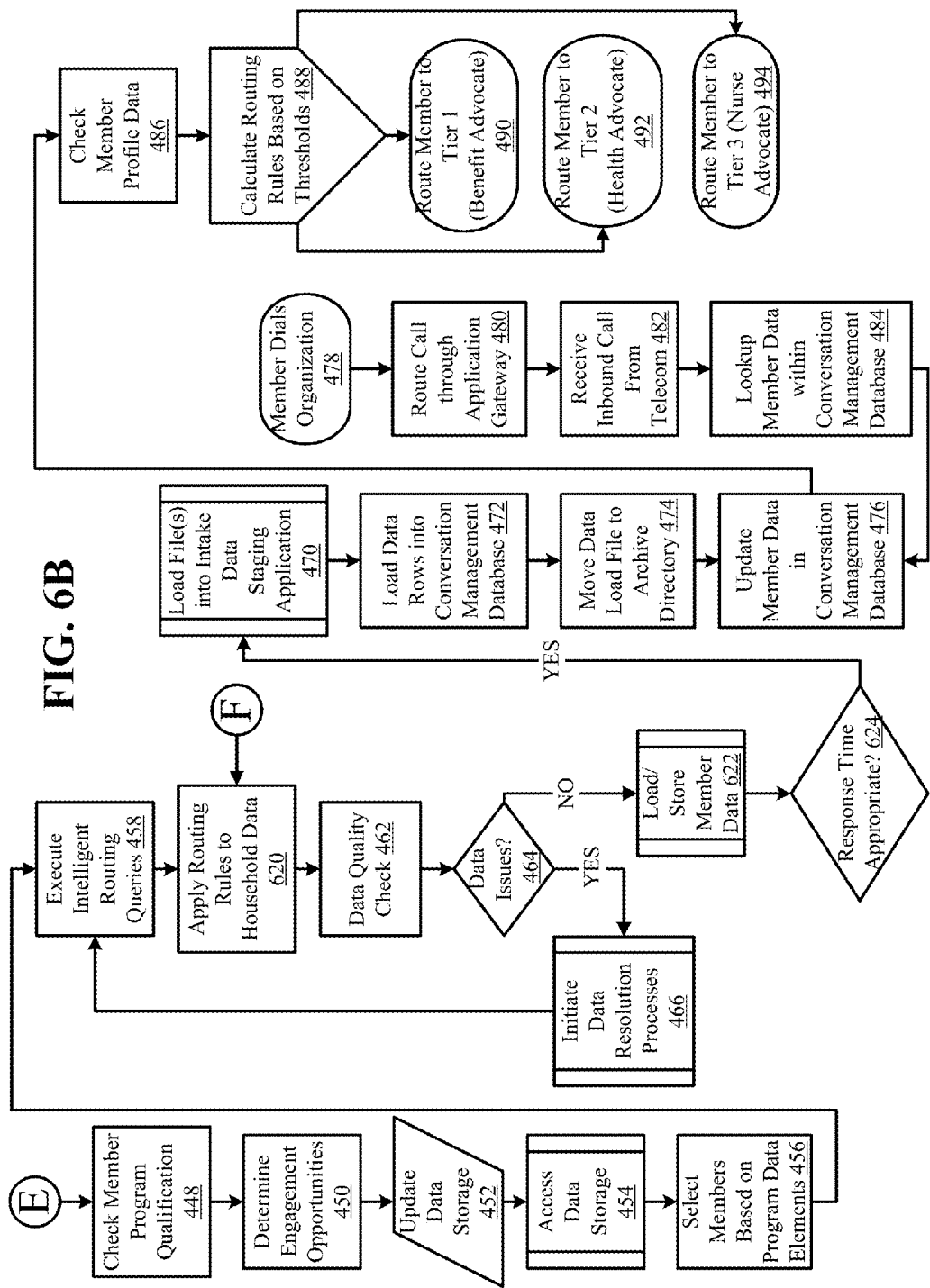
Figure 6C:
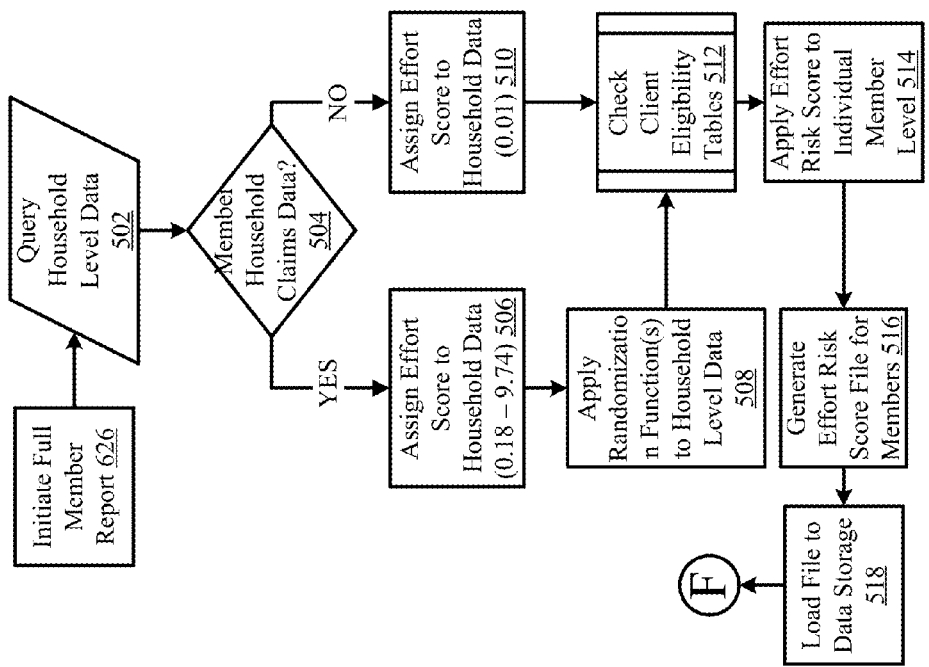

FIGS. 6A through 6C illustrate a further embodiment of the method of FIGS. 4A through 4C for intelligent routing of a member of an organization to an appropriate organization advocate within a network. The reference numbers used in FIGS. 4A through 4C are maintained for identical steps illustrated within FIGS. 6A through 6C. Since the methods of FIGS. 4A through 4C and FIGS. 6A through 6C are substantially identical, only the differences between the figure sets is described in detail below.

As illustrated in FIG. 6B, after step 458, routing rules are applied to member household level data (illustrated as 620). For example, household data may be aggregated to compare Tier 3 routing thresholds that determine Tier 3 routing. If Tier 3 routing thresholds are not surpassed, Tier 2 (effort risk score) is considered for Tier 2 member household routing. If no Tier 2 routing is required, the member household data may be routed to Tier 1 using default routing. The data check (illustrated as 462) may involve the performance of data integrity validations. Examples of integrity validations include, for example, looking for null data elements or duplication of data fields.

Still referring to FIG. 6B, if it is determined that the household data does not have any issues after the quality check is performed (illustrated as 464), the household member data is loaded/stored (illustrated as 622) and it is determined whether the loading response time was appropriate (illustrated as 624). The conversation management processor 110 may query the loaded household member data, and therefore an appropriate time of loading may be real-time or substantially real-time. If the response time is determined appropriate, a routing file is generated for the household member data, and the file is loaded into the intake data staging application (illustrated as 470). For example, it may be possible to utilize files from the source system and calculate the rules in real time. However files are used after the calculations have already been made to define the advocate Tier when the time to do real-time processing back to multiple sources systems takes too long. The amount of time that is too long is based on what the organization has defined as the speed a member call needs to be answered.

As illustrated in FIG. 6C, a full member report is initiated (illustrated as 626) prior to the household level data being queried at step 502. The full report may be a file for employer and individual (E & I) members used to calculate effort risk scores. Furthermore, as illustrated in FIG. 6C, the embodiment of FIGS. 6A through 6C omit steps 520-528 of FIGS. 4A through 4C. This results in step 620 described above following step 518.

Although aspects of the present disclosure are described with respect to embodiments in a healthcare context, it should be understood that various disclosed techniques can be used in numerous other fields of technology in which intelligent routing involves sensitive information. Various applications of the disclosed techniques provide substantial improvements to the functioning of the computer apparatus and the technical environments in which the various applications are implemented.

Moreover, although the present disclosure has been described herein with reference to the accompanying drawings, it is to be understood that the present disclosure is not limited to those precise teachings, and that various other changes and modifications may be made by one skilled in the art without departing from the spirit and scope of the present disclosure.

What is claimed is:

1. A secure network for intelligently routing an organization's member to an organization representative, comprising:
    an authentication processor configured to authenticate the member using automatic number identification;
    a natural language processor configured to provide the member with one or more open-ended questions and to analyze spoken content of the member to determine an explicit need of the member based on the spoken content being responsive to the one or more open-ended questions; and
    a conversation management processor configured to:
    determine an implicit need of the member, the implicit need of the member being based on member household data, the member household data including cumulative data for each of the individuals residing in a household of the member, determining the implicit need being further based on a referral score and an effort risk score for the member;
    determine the referral score based in part on the household data, to correspond to a propensity of the member to contact the organization regarding a program for which the member's household is eligible;
    determine the effort risk score to correspond to a likelihood of an individual in the member's household being eligible for a program of the organization, all the individuals of the household receiving a same effort risk score; and
    determine a tier of organization representatives to route the member to based on the explicit need of the member determined by the natural language processor and the implicit need of the member determined via the member household data.

2. The secure network of claim 1, wherein determining the tier of the organization representatives comprises:

routing the member to a third tier representative when the member household data satisfies at least one third tier routing rule, the at least one third tier routing rule comprising:
   a monetized value of the member household data is greater than a first threshold value; and
   a cost risk score of the member household data is greater than a second threshold value, wherein the cost risk score is based on claims data;
routing the member to a second tier representative when the member household data satisfies at least one second tier routing rule, the at least one second tier routing rule comprising:
   an effort risk score of the member household data is greater than a third threshold, the effort risk score corresponding to a likelihood of the member being eligible for a program of the organization; and
   the monetized value of the member household data is between a fourth threshold and a fifth threshold; and
routing the member to a first tier representative when the member is not routed to the third tier representative or the second tier representative.

3. The secure network of claim 1, wherein an effort risk score of about 0.01 results in the member being routed to a first tier representative.

4. The secure network of claim 1, wherein the referral score is derived from multiple variables, including at least one of pharmacy first-fill data, treatment decision support (TDS) program referral data, a pharmacy value factor score, an impact pro cost risk score, a comprehensive medication review (CMR) program data, and a cost risk score based on claims data, and
   and the household data upon which the effort risk score is based includes at least one of medical claims data and pharmacy claims data for each individual in the member's household.

5. A method for intelligently routing a member of an organization to an organization representative, comprising:
   providing at least one open-ended question to a member;
   receiving a communication from the member, the communication including spoken words;
   determining an identity of the member;
   determining an explicit need of the member represented in the spoken words via natural language processing, the spoken words being responsive to the at least one open-ended question;
   determining an implicit need of the member using cumulative household data for each of the individuals residing in the member's household;
   determining an organization representative to route the member to based on the explicit need of the member determined via natural language processing and the implicit need of the member determined via the household data, wherein determining the implicit need of the member comprises determining a referral score and an effort risk score for the member,
   the referral score being determined for the member based in part on the household data, and corresponding to a propensity of the member to contact the organization regarding a program for which the member is eligible, and
   the effort risk score being based in part on the household data and corresponding to a likelihood of the member's household being eligible for a program of the organization, all the individuals of the household receiving a same effort risk score.

6. The method of claim 5, wherein determining the organization representative comprises routing the member to a third tier representative when the household data includes either a monetized value that is greater than a first threshold value or a cost risk score based on claims data that is greater than a second threshold value.

7. The method of claim 5, wherein the referral score is derived from multiple variables, including at least one of pharmacy first-fill data, treatment decision support (TDS) program referral data, a pharmacy value factor score, an impact pro cost risk score, a comprehensive medication review (CMR) program data, and a cost risk score based on claims data, and
   and the household data upon which the effort risk score is based includes at least one of medical claims data and pharmacy claims data for each individual in the member's household.

8. The method of claim 6, wherein determining the organization representative comprises routing the member to a second tier representative when the effort risk score is greater than a third threshold.

9. The method of claim 8, wherein determining the organization representative comprises routing the member to a first tier representative when the member is not routed to the third tier representative or the second tier representative.

10. A system for intelligently routing an organization's member to an organization representative, comprising:
   an authentication processor configured to authenticate the member;
   a natural language processor configured to provide the member with at least one open-ended question and to analyze spoken content of the member to determine an explicit need of the member, the spoken content being responsive to the at least one open-ended question;
   a conversation management processor configured to:
      analyze member household data to generate an implicit need of the member, the household data being cumulative data for each of the individuals in the member's household, and the implicit need being based on a referral score and an effort risk score for the member,
         the referral score being determined for the member based in part on the household data, and corresponding to a propensity of the member to contact the organization regarding a program for which the member is eligible, and
         the effort risk score being and corresponding to a likelihood of the member's household being eligible for a program of the organization, all the individuals of the household receiving a same effort risk score; and
      route the member to a tier of organization representatives based on the explicit need of the member determined via the natural language processor and the implicit need of the member determined via the member household data.

11. The system of claim 10, wherein the member is routed to a second tier representative when the effort risk score is greater than a threshold.

12. The system of claim 10, wherein the member is routed to a first tier representative when the effort risk score is about 0.01.

13. The system of claim 10, wherein the conversation management processor generates the referral score by, in part, analyzing historical and present member household data with respect to at least one program eligibility table.

14. The system of claim 13, wherein the historical member household data relates to activities that occurred prior to the member becoming a member of the organization, and wherein the present member household data relates to activities occurring after the member became a member of the organization.

15. The system of claim 10, wherein the member is routed to either a second tier representative or a third tier representative when the effort risk score is about 0.18 to about 9.74.

16. The system of claim 10, wherein routing the member to a tier of organization representatives based on thresholds includes:
routing the member to a third tier representative when either a monetized value of the member household data is greater than a first threshold value or a cost risk score of the member household data is greater than a second threshold value;
routing the member to a second tier representative when the effort risk score of the member household data is greater than a third threshold or the monetized value of the member household data is between a fourth threshold and a fifth threshold; and
routing the member to a first tier representative when the member is not routed to the third tier representative or the second tier representative.

17. The system of claim 10, wherein the referral score is derived from multiple variables, including at least one of pharmacy first-fill data, treatment decision support (TDS) program referral data, a pharmacy value factor score, an impact pro cost risk score, a comprehensive medication review (CMR) program data, and a cost risk score based on claims data, and
and the household data upon which the effort risk score is based includes at least one of medical claims data and pharmacy claims data for each individual in the member's household.

* * * * *

UNITED STATES PATENT AND TRADEMARK OFFICE
CERTIFICATE OF CORRECTION

PATENT NO. : 9,860,382 B2  
APPLICATION NO. : 14/936874  
DATED : January 2, 2018  
INVENTOR(S) : Mazed et al.

Page 1 of 1

It is certified that error appears in the above-identified patent and that said Letters Patent is hereby corrected as shown below:

On the Title Page

ADD:  
(72) Inventor: Lawrence Kevin Sundberg, Big Lake, MI (US);

Signed and Sealed this  
Sixteenth Day of March, 2021

Drew Hirshfeld  
*Performing the Functions and Duties of the*  
*Under Secretary of Commerce for Intellectual Property and*  
*Director of the United States Patent and Trademark Office*